(12) United States Patent
Uehara

(10) Patent No.: US 8,258,302 B2
(45) Date of Patent: Sep. 4, 2012

(54) METHOD FOR PRODUCING BENZAZEPINONE

(75) Inventor: Hisatoshi Uehara, San Diego, CA (US)

(73) Assignee: API Corporation, Osaka (JP)

( * ) Notice: Subject to any disclaimer, the term of this patent is extended or adjusted under 35 U.S.C. 154(b) by 874 days.

(21) Appl. No.: 12/162,553

(22) PCT Filed: Jan. 31, 2007

(86) PCT No.: PCT/JP2007/051577
§ 371 (c)(1),
(2), (4) Date: Nov. 12, 2008

(87) PCT Pub. No.: WO2007/088878
PCT Pub. Date: Aug. 9, 2007

(65) Prior Publication Data
US 2009/0171090 A1      Jul. 2, 2009

(30) Foreign Application Priority Data

Jan. 31, 2006   (JP) ................... 2006-023518

(51) Int. Cl.
C07D 217/00 (2006.01)
C07D 217/22 (2006.01)
A01N 43/42 (2006.01)
A61K 31/47 (2006.01)

(52) U.S. Cl. ......... 546/139; 546/141; 514/307; 514/309

(58) Field of Classification Search ........................ None
See application file for complete search history.

(56) References Cited

U.S. PATENT DOCUMENTS

| 4,182,758 | A | 1/1980 | Kamiya et al. |
| 4,415,496 | A | 11/1983 | Harris et al. |
| 5,183,921 | A | 2/1993 | Takase et al. |
| 5,389,619 | A | * | 2/1995 | Doetzer et al. ................. 514/63 |
| 2004/0077627 | A1 | 4/2004 | Koenig et al. |
| 2004/0248878 | A1 | 12/2004 | Koenig et al. |
| 2005/0261495 | A1 | 11/2005 | Audia et al. |

FOREIGN PATENT DOCUMENTS

| EP | 0 061 187 | 9/1982 |
| EP | 0 468 775 | 1/1992 |
| FR | 2 474 505 | 7/1981 |
| JP | 2002-518483 | 6/2002 |
| JP | 2004-517090 | 6/2004 |
| JP | 2004-521084 | 7/2004 |
| JP | 2005-538031 | 12/2005 |
| WO | 99/66934 | 12/1999 |
| WO | 99/67221 | 12/1999 |
| WO | 02/47671 | 6/2002 |

OTHER PUBLICATIONS

Brienne, MJ. 66. Synthesis of Chiral Bicyclic Bis-lactam Components for the Controlled Self-Assembly of Hydrogen-Bonded Arrays. Helvetica Chimica Acta. 1997, vol. 80, p. 859.*
Yu, Y. A regioselective synthesis of 3-benzazepinones via intramolecular hydroamidation of acetylenes. Tetrahedron Letters. 2006, vol. 47, p. 3812, table 1.*
Rompaey, KV. et al. A versatile synthesis of 2-substituted 4-amino-1,2,4,5-tetrahydro-2-benzazepine-3-ones. Tetrahedron. 2003, vol. 59, p. 4424.*
Reby, C. et al. Reduction of quaternary ammonium salts of 1-aroyldihydroisoquinoline by zinc in acid media. Access to 2-aryltetrahydro-3-benzazepines. Bulletin de la Societe Chimique de France. 1972, vol. 4, p. 1574.*
Mitchell, David et al., Classical and dynamic resolution of 1-amino-3-ethyl-1,3,4,5-tetrahydrobenzo[d]azepin-2-one, Tetrahedron: Asymmetry, 2005, vol. 16, No. 23, pp. 3814-3819.
Mistryukov, Electron A. et al., Lewis acid mediated cyclization of beta-phenylethylamides with an unactivated benzene ring: an efficient preparation of dihydroisoquinolines, Mendeleev Communications, 1996, No. 6, pp. 239-241.
Ben-Ishai et al., "Intra vs. Intermolecular Amidoalkylation of Aromatics," Tetrahedron, vol. 43, No. 2, pp. 439-450 (1987).
Ishibashi et al., "A Convenient Synthesis of 1, 3, 4, 5-Tetrahydro-2H-3-benzazepin-2-ones by Acid-Catalyzed Cyclization of N-(2-Arylethyl)-N-methyl-2-sulfinylacetamides," Chemical and Pharmaceutical Bulletin, vol. 37, No. 4, pp. 939-943 (1989).
Baudoin et al., "Application of the Palladium Catalyzed Borylation/Suzuki Coupling (BSC) Reaction to the Synthesis of Biologically Active Biaryl Lactams," Journal of Organic Chemistry, vol. 67, pp. 1199-1207 (2002).
Haeusler et al., "Ringöffnungen von 1,2-Didehydroprolinnen, I. Darstellung von 4-Hydroxyornithin and geschützten 4-Amino-3-hydroxybutyronitrilen" Liebigs Annalen Der Chemie, vol. 12, pp. 1231-1237, 1992.
Tijhaus et al. "A Practical Synthesis of N-Hydroxy-α-amino Acid Derivatives" Sythesis, vol. 11, pp. 890-893, 1980.
Lau et al., "Association phenomena. 3. Polyfunctional catalysis of acetyl phosphate decomposition" Journal of the American Chemical Society, vol. 100, No. 6, pp. 1857-1865, 1978.
Murakata et al., "Oxidative cyclisation of o-phenolic oxime-acid derivatives using phenyliodonium diacetate: synthesis of spiroisoxazoline derivatives" Tetrahedron, vol. 52, No. 47, pp. 14713-14722, 1996.
Yanagisawa et al., "Angiotensin-Converting Enzyme Inhibitors. Perhydro-1,4-thiazepin-5-one Derivatives", Journal of Medicinal Chemistry, vol. 30, No. 11, pp. 1984-1991, 1987.
Extended European Search report issued with respect to European Patent Application No. 07707779.0, dated Nov. 15, 2011.

* cited by examiner

Primary Examiner — Rita Desai
Assistant Examiner — Ben S Michelson
(74) Attorney, Agent, or Firm — Greenblum & Bernstein, P.L.C.

(57) ABSTRACT

It is an object of the present invention to provide 2-iminocarboxylic acid derivatives, and a practically suitable industrial method for producing benzazepinones in a short process under mild conditions. The present invention provides a method for producing a benzazepinone or a salt thereof, which comprises opening a ring of an isoquinoline derivative and subsequently converting the thus generated amine into a benzazepinone through lactamization reaction.

7 Claims, No Drawings

METHOD FOR PRODUCING BENZAZEPINONE

TECHNICAL FIELD

The present invention relates to novel 2-iminocarboxylic acid derivatives which are useful as intermediates of pharmaceuticals, agrochemicals or the like, and an industrial method for producing subsequent intermediates, benzazepinones using such derivatives. Benzazepinones produced by the present invention can be derivatized into useful drugs as therapeutic agents for Alzheimer's disease via an optically active 1-aminobenz[d]azepin-2-ones or the like.

BACKGROUND ART

The benzazepinones produced by the method of the present invention are compounds of seven-membered lactam rings fused to benzene rings. In contrast with five- or six-membered rings fused to benzene rings, the formation of which is often reported and is comparatively readily attained, such seven-membered rings found in benzazepinones are very difficult to form, and methods using carbon-carbon bond formation within aromatic rings need specific substrates or harsh reaction conditions.

For example, as methods for synthesizing benzazepinones, methods in which 1-aminoazepin-2-one derivatives are synthesized through intramolecular cyclization reaction of bis (methoxycarbonylamino)acetic acid derivatives (see Non-patent Document 1, for example) are known. However, such methods require special and expensive bis(alkoxycarbonylamino)acetic acid, and thus are not appropriate methods in terms of industry. Moreover, a method in which sulfuric acid and a phenylacetylamide derivative having dimethylacetal are treated at high temperature to form an azepinone ring through intramolecular cyclization reaction, followed by oxidation of the 1-position and a method in which aluminum chloride and 2-chloro-N-phenethyl-N-methylacetamide are treated at high temperature to form an azepinone ring through intramolecular Friedel-Crafts reaction, followed by oxidation of the 1-position (see Patent Document 1, for example) are also known. However, all of these methods need harsh conditions at excessively high temperatures with highly reactive reagents, and thus are considered to be difficult to control in terms of industry. Moreover, the 1-position has to be oxidized after the cyclization, and therefore these methods can hardly be efficient.

Furthermore, as a method for synthesizing benzazepinones under relatively mild conditions, a method which use cyclization reaction of Pummerer type rearrangement with sulfoxides is reported (see Non-patent Document 2, for example). However, this method requires many steps for introducing and removing sulfoxides and uses expensive periodates, and thus can hardly be appropriate methods in terms of industry.

On the other hand, a method in which an azepinone ring is formed through amide bond formation, is also reported. However, expensive reagents are required for a method in which an azepinone ring is formed after forming a biaryl compound through Suzuki coupling reaction (see Non-patent Document 3, for example). Moreover, a method in which an azepinone ring is formed after carboxylation (see Patent Document 2, for example) is also known. However, this method requires cryogenic reaction using a strong base for the carboxylation, and thus can not be inexpensive industrial production methods. Moreover, all cases are limited to dibenz[b,d]azepin-2-one skeletons, and the 1-position has to be oxidized. Therefore, these methods are not versatile and inefficient.

Patent Document 1: PCT International Publication No. WO 2002/47671

Patent Document 2 PCT International Publication No. WO 1999/66934

Non-patent Document 1: Tetrahedron, 1987, 43, 439.

Non-patent Document 2: Chem. Pharm. Bull., 1989, 37, 939.

Non-patent Document 3: J. Org. Chem., 2002, 67, 1199.

DISCLOSURE OF THE INVENTION

Object to be Solved by the Invention

It is an object of the present invention to provide 2-iminocarboxylic acid derivatives, and a practically suitable industrial method for producing benzazepinones in a short process under mild conditions.

Means for Solving the Object

In order to solve the above object, the inventors of the present invention have conducted intensive studies. As a result, they have found that 2-iminocarboxylic acid derivatives can be synthesized by treating readily-synthesizable isoquinoline derivatives of six-membered rings fused to benzene rings, with an amine or a salt thereof, and further lactamization thereof enables efficient synthesis of benzazepinones which are compounds of seven-membered rings fused to benzene rings, in a short process under mild conditions. This has led to the completion of the present invention.

Specifically, the present invention provides the following inventions.

[1] A method for producing a benzazepinone represented by the following formula (2), or a salt thereof, which comprises: opening a ring of an isoquinoline derivative represented by the following formula (1): and subsequently converting the thus generated amine into a benzazepinone through lactamization reaction.

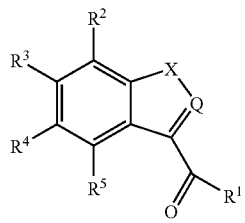

(1)

wherein $R^1$ represents an alkoxy group, an aryloxy group, an alkylthio group, an arylthio group, or an amino group; each of $R^2$ to $R^5$ independently represents a hydrogen atom, an alkoxy group, an amino group, a halogen atom, a cyano group, a nitro group, or an alkyl group or an aryl group containing 1 to 10 carbon atoms; X represents an ethylene group, an ethenylene group, or an arylene group; and Q is a tertiary or quaternary nitrogen atom, which, in those cases of a quaternary form, is substituted with an alkyl group or an aryl group containing 1 to 10 carbon atoms and has counter ion(s) $Y^-$, wherein $Y^-$ represents a halide ion, an inorganic acid ion, an alkylsulfate ion, a mesylate ion, a tosylate ion, an alkylsulfonate ion, an organic acid ion, and/or a hydroxide ion, and a plurality of counter ions may be held in combination;

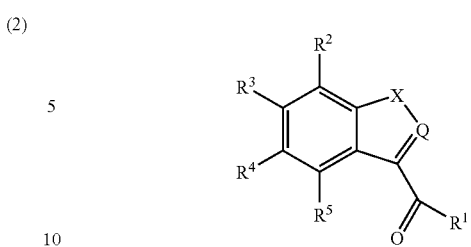

wherein $R^1$ represents an alkoxy group, an aryloxy group, an alkylthio group, an arylthio group, or an amino group; each of $R^2$ to $R^5$ independently represents a hydrogen atom, an alkoxy group, an amino group, a halogen atom, a cyano group, a nitro group, or an alkyl group or an aryl group containing 1 to 10 carbon atoms; X represents an ethylene group, an ethenylene group, or an arylene group; and Q is a tertiary or quaternary nitrogen atom, which, in those cases of a quaternary form, is substituted with an alkyl group or an aryl group containing 1 to 10 carbon atoms and has counter ion(s) $Y^-$, wherein $Y^-$ represents a halide ion, an inorganic acid ion, an alkylsulfate ion, a mesylate ion, a tosylate ion, an alkylsulfonate ion, an organic acid ion, and/or a hydroxide ion, and a plurality of counter ions may be held in combination;

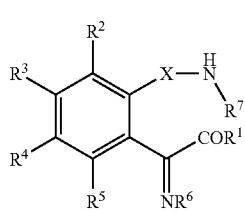

wherein $R^1$ to $R^5$ and X have the same definitions as described below; $R^6$ represents a hydrogen atom, a hydroxyl group, an alkoxy group, an aryloxy group, an amino group, or an alkyl group or an aryl group containing 1 to 10 carbon atoms; and $R^7$ represents a hydrogen atom, or an alkyl group or an aryl group containing 1 to 10 carbon atoms.

[5] A method for producing a benzazepinone represented by the following formula (2) or a salt thereof, which comprises lactamizing a 2-iminocarboxylic acid derivative represented by the following formula (3) or a salt thereof:

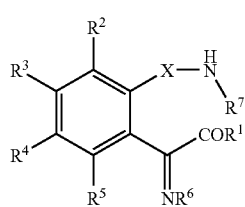

wherein $R^1$ represents an alkoxy group, an aryloxy group, an alkylthio group, an arylthio group, or an amino group; each of $R^2$ to $R^5$ independently represents a hydrogen atom, an alkoxy group, an amino group, a halogen atom, a cyano group, a nitro group, or an alkyl group or an aryl group containing 1 to 10 carbon atoms; $R^6$ represents a hydrogen atom, a hydroxyl group, an alkoxy group, an aryloxy group, an amino group, or an alkyl group or an aryl group containing

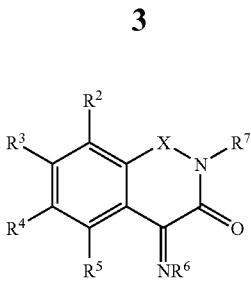

wherein $R^2$ to $R^5$ and X have the same definitions as described above; $R^6$ represents a hydrogen atom, a hydroxyl group, an alkoxy group, an aryloxy group, an amino group, or an alkyl group or an aryl group containing 1 to 10 carbon atoms; and $R^7$ represents a hydrogen atom, or an alkyl group or an aryl group containing 1 to 10 carbon atoms,

[2] A method for producing an aminobenzazepinone or a salt thereof, which comprises: a step of producing a benzazepinone represented by the following formula (2) or a salt thereof through the method according to [1]; and a step of reducing the benzazepinone represented by the formula (2) or the salt thereof which has been produced in the above manner, to thereby convert into an aminobenzazepinone represented by the following formula (4):

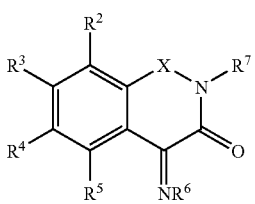

wherein each of $R^2$ to $R^5$ independently represents a hydrogen atom, an alkoxy group, an amino group, a halogen atom, a cyano group, a nitro group, or an alkyl group or an aryl group containing 1 to 10 carbon atoms; $R^6$ represents a hydrogen atom, a hydroxyl group, an alkoxy group, an aryloxy group, an amino group, or an alkyl group or an aryl group containing 1 to 10 carbon atoms; $R^7$ represents a hydrogen atom, or an alkyl group or an aryl group containing 1 to 10 carbon atoms; and X represents an ethylene group, an ethenylene group, or an arylene group,

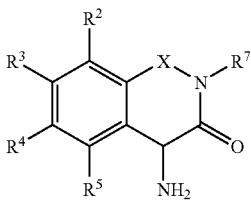

wherein $R^2$ to $R^5$, $R^7$, and X have the same definitions as described above.

[3] The method according to [2], which further comprises resolving the aminobenzazepinone into an optically active aminobenzazepinone.

[4] A method for producing a 2-iminocarboxylic acid derivative represented by the following formula (3) or a salt thereof, which comprises reacting an isoquinoline derivative represented by the following formula (1) with an amine or a salt thereof.

1 to 10 carbon atoms; $R^7$ represents a hydrogen atom, or an alkyl group or an aryl group containing 1 to 10 carbon atoms; and X represents an ethylene group, an ethenylene group, or an arylene group.

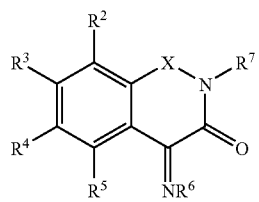

(2)

wherein $R^2$ to $R^7$ and X have the same definitions as described below;

[6] A 2-iminocarboxylic acid derivative represented by the following formula (3) or a salt thereof.

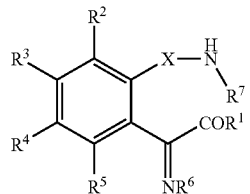

(3)

wherein $R^1$ represents an alkoxy group, an aryloxy group, an alkylthio group, an arylthio group, or an amino group; each of $R^2$ to $R^5$ independently represents a hydrogen atom, an alkoxy group, an amino group, a halogen atom, a cyano group, a nitro group, or an alkyl group or an aryl group containing 1 to 10 carbon atoms; $R^6$ represents a hydrogen atom, a hydroxyl group, an alkoxy group, an aryloxy group, an amino group, or an alkyl group or an aryl group containing 1 to 10 carbon atoms; $R^7$ represents a hydrogen atom, or an alkyl group or an aryl group containing 1 to 10 carbon atoms; and X represents an ethylene group, an ethenylene group, or an arylene group.

[7] A 3,4-dihydroisoquinolinium salt represented by the following formula (1a):

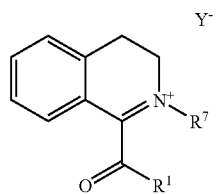

(1a)

wherein $R^1$ represents an alkoxy group, an aryloxy group, an alkylthio group, an arylthio group, or an amino group; $R^7$ represents a hydrogen atom, or an alkyl group or an aryl group containing 1 to 10 carbon atoms; and $Y^-$ represents a halide ion, an inorganic acid ion, an alkylsulfate ion, a mesylate ion, a tosylate ion, an alkylsulfonate ion, an organic acid ion, and/or a hydroxide ion, and a plurality of counter ions may be held in combination.

BEST MODE FOR CARRYING OUT THE INVENTION

Hereafter, the present invention will be described in detail.

<Method for Producing Benzazepinone>

The present invention relates to a method for producing a benzazepinone represented by the following formula (2) or a salt thereof, which comprises opening a ring of an isoquinoline derivative represented by the following formula (1) through cleavage of the carbon-nitrogen double bond; and subsequently converting the thus generated amine into a benzazepinone through lactamization reaction.

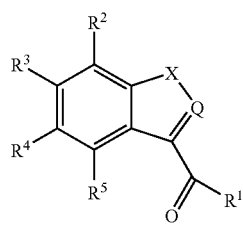

(1)

wherein $R^1$ to $R^5$, Q, X, and $Y^-$ have the same definitions as described above;

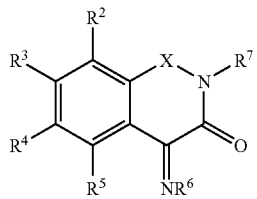

(2)

wherein $R^2$ to $R^7$ and X have the same definitions as described above.

The isoquinoline derivative represented by the above formula (1) is a compound in which the 1-position is substituted with a carbonyl group, including isoquinolines, 3,4-dihydroisoquinolines, and phenanthridines having a tertiary nitrogen atom at the 2-position, and isoquinolinium salts, 3,4-dihydroisoquinolinium salts, and phenanthridinium salts having a quaternary nitrogen atom substituted with an alkyl group or an aryl group at the 2-position. In cases where there is a quaternary nitrogen atom at the 2-position, the isoquinoline derivative represented by the above formula (1) is an ionic compound and has counter ion(s) $Y^-$.

In the above formula (1), $R^1$ represents an alkoxy group, an aryloxy group, an alkylthio group, an arylthio group, or an amino group, which may have a substituent group.

Specific examples of the alkoxy group include, but not limited to: linear alkoxy groups such as a methoxy group, an ethoxy group, a propoxy group, and a butoxy group; cyclic alkoxy groups such as a cyclopentyloxy group and a cyclohexyloxy group; branched alkoxy groups such as an isopropoxy group, a 1-methylpropyloxy group, and a t-butoxy group; and substituted alkoxy groups such as a benzyloxy group and a 2-chloroethoxy group.

Specific examples of the aryloxy group include, but not limited to: a phenoxy group; and substituted aryloxy groups such as a 4-chlorophenoxy group, a pentafluorophenoxy group, and a 2-nitrophenoxy group.

Specific examples of the alkylthio group include, but not limited to: linear alkylthio groups such as a methylthio group, an ethylthio group, a propylthio group, and a butylthio group; cyclic alkylthio groups such as a cyclopentylthio group and a cyclohexylthio group; branched alkylthio groups such as an isopropylthio group, a 1-methylpropylthio group, and a t-butylthio group; and substituted alkylthio groups such as a benzylthio group and a 2-chloroethylthio group.

Specific examples of the arylthio group include, but not limited to: phenylthio groups; and substituted arylthio groups such as a 4-chlorophenylthio group, a pentafluorophenylthio group, and a 2-nitrophenylthio group.

Specific examples of the amino group include, but not limited to: an unsubstituted amino group; primary amino groups such as a methylamino group, an ethylamino group, an isopropylamino group, a cyclohexylamino group, and an anilino group; secondary amino groups such as a dimethylamino group, a diethylamino group, a diisopropylamino group, a methylpropylamino group, and a dicyclohexylamino group; substituted alkylamino groups such as a benzylamino group and a 2-cyanoethylamino group; substituted arylamino groups such as a 4-methoxyphenylamino group and a 4-chlorophenylamino group; cyclic amino groups such as a piperidino group and a morpholino group; a hydroxyamino group; alkoxyamino groups such as a methoxyamino group and a benzyloxyamino group; and a hydrazino group.

Of these, preferred are alkoxy groups which can be synthesized from an inexpensive oxalic diester and which allow subsequent cyclization reaction to readily proceed, more preferred are linear alkoxy groups such as a methoxy group, an ethoxy group, a propoxy group, and a butoxy group, and particularly preferred are a methoxy group and an ethoxy group.

Each of $R^2$ to $R^5$ independently represents a hydrogen atom, an alkoxy group, an amino group, a halogen atom, a cyano group, a nitro group, or an alkyl group or an aryl group containing 1 to 10 carbon atoms. Moreover, a plurality of adjacent $R^2$ to $R^5$ may unitedly form a ring structure.

The alkoxy group may have a substituent group. Specific examples thereof include, but not limited to: linear alkoxy groups such as a methoxy group, an ethoxy group, a propoxy group, and a butoxy group; cyclic alkoxy groups such as a cyclopentyloxy group and a cyclohexyloxy group; branched alkoxy groups such as an isopropoxy group, a 1-methylpropyloxy group, and a t-butoxy group; and substituted alkoxy groups such as a benzyloxy group and a 2-chloroethoxy group.

The amino group may have a substituent group. Specific examples thereof include, but not limited to: an unsubstituted amino group; primary amino groups such as a methylamino group, an ethylamino group, an isopropylamino group, a cyclohexylamino group, and an anilino group; secondary amino groups such as a dimethylamino group, a diethylamino group, a diisopropylamino group, a methylpropylamino group, and a dicyclohexylamino group; substituted alkylamino groups such as a benzylamino group and a 2-cyanoethylamino group; substituted arylamino groups such as a 4-methoxyphenylamino group and a 4-chlorophenylamino group; cyclic amino groups such as a piperidino group and a morpholino group; a hydroxyamino group; and alkoxyamino groups such as a methoxyamino group and a benzyloxyamino group.

Specific examples of the halogen atom include a fluorine atom, a chlorine atom, a bromine atom, and an iodine atom.

The alkyl group or the aryl group containing 1 to 10 carbon atoms may be substituted, and the alkyl group may take any of a linear form, a cyclic form, and a branched form. Specific examples of the alkyl group or the aryl group include, but not limited to: linear alkyl groups such as a methyl group, an ethyl group, a propyl group, and a butyl group; cyclic alkyl groups such as a cyclopentyl group and a cyclohexyl group; branched alkyl groups such as an isopropyl group, a 1-methylpropyl group, and a t-butyl group; aryl groups such as a phenyl group and a piperonyl group; and heteroaryl groups such as a pyridyl group and a thienyl group. These groups may be arbitrarily substituted to the extent that the reaction of the present invention is not affected.

The type of the substituent group of the alkyl group or the aryl group is not particularly limited. Specific examples thereof include: halogen atoms such as fluorine, chlorine, and bromine; linear, cyclic, or branched alkyl groups such as a methyl group, an ethyl group, a cyclohexyl group, and an isopropyl group; aryl groups such as a phenyl group and a piperonyl group; heteroaryl groups such as a pyridyl group and a thienyl group; alkoxy groups such as a methoxy group, an ethoxy group, a phenoxy group, and an isopropoxy group; a cyano group; and a nitro group.

Specific examples of the plurality of adjacent $R^2$ to $R^5$ which unitedly form a ring structure include, but not limited to: a methylenedioxy group, an ethylenedioxy group, a carbonyldioxy group, an ureylene group, a trimethylene group, a tetramethylene group, fused benzene rings, fused furan rings, and fused imidazole rings.

Of these, preferred are a hydrogen atom, an alkoxy group, and a halogen atom. More preferred are a hydrogen atom, a methoxy group, an ethoxy group, a benzyloxy group, a fluorine atom, and a chlorine atom. Particularly preferred is a hydrogen atom which allows derivatization into an optically active 1-amino-3-methyl-1,3,4,5-tetrahydrobenz[d]azepin-2-one which is useful as an intermediate of therapeutic agents for Alzheimer's disease.

Regarding the combination of $R^2$ to $R^5$, three or more of them are preferably hydrogen atoms, and more preferably, all four are hydrogen atoms.

Q is a tertiary or quaternary nitrogen atom, which, in those cases of a quaternary form, is substituted with an alkyl group or an aryl group containing 1 to 10 carbon atoms and has counter ion(s) $Y^-$. Here, the alkyl group or the aryl group containing 1 to 10 carbon atoms may be substituted, and the alkyl group may take any of a linear form, a cyclic form, and a branched form. Specific examples of the alkyl group or the aryl group include, but not limited to: linear alkyl groups such as a methyl group, an ethyl group, a propyl group, and a butyl group; cyclic alkyl groups such as a cyclopentyl group and a cyclohexyl group; branched alkyl groups such as an isopropyl group, a 1-methylpropyl group, and a t-butyl group; aryl groups such as a phenyl group and a piperonyl group; and heteroaryl groups such as a pyridyl group and a thienyl group. Of these, preferred Q is a quaternary nitrogen atom substituted with a linear alkyl group that can be readily synthesized by using an alkylating agent. More preferred is a quaternary nitrogen atom substituted with a methyl group or an ethyl group that can be derivatized from dimethyl sulfate or diethyl sulfate of industrially inexpensive prices. Particularly preferred is a quaternary nitrogen atom substituted with a methyl group which allows derivatization into an optically active 1-amino-3-methyl-1,3,4,5-tetrahydrobenz[d]azepin-2-one which is useful as an intermediate of therapeutic agents for Alzheimer's disease. These substituent groups of the quaternary nitrogen atom may be arbitrarily substituted to the extent that the reaction of the present invention is not affected.

The type of the substituent group is not particularly limited. Specific examples thereof include: halogen atoms such as fluorine, chlorine, and bromine; linear, cyclic, or branched alkyl groups such as a methyl group, an ethyl group, a cyclopropyl group, a cyclohexyl group, and an isopropyl group; aryl groups such as a phenyl group and a piperonyl group; heteroaryl groups such as a pyridyl group and a thienyl group; alkoxy groups such as a methoxy group, an ethoxy group, and an isopropoxy group; a cyano group; and a nitro group. Preferred specific examples of the substituent group of the quaternary nitrogen atom having a substituent group include a trifluoromethyl group, a 2,2,2-trifluoroethyl group, a cyclopropylmethyl group, a benzyl group, a 2-(4-methoxyphenyl) ethyl group, and a 3-chlorophenyl group.

Specific examples of the counter ion $Y^-$ include, but not limited to: halide ions such as a chloride ion, a bromide ion, and an iodide ion; inorganic acid ions such as a sulfate ion, a hydrogen sulfate ion, and a nitrate ion; alkylsulfate ions such as a methylsulfate ion and an ethylsulfate ion; alkylsulfonate ions such as a mesylate ion, a tosylate ion, and a trifluoromethanesulfonate ion; organic acid ions such as an acetate ion and an oxalate ion; and a hydroxide ion, and a plurality of counter ions may be held in combination. Of these, preferred are halide ions, alkylsulfate ions, and alkylsulfonate ions which are counter ions generated from alkylating agents. More preferred are alkylsulfate ions generated from dialkyl sulfate which is an inexpensive alkylating agent. Particularly preferred is an methylsulfate ion generated from dimethyl sulfate to be used for synthesizing an optically active 1-amino-3-methyl-1,3,4,5-tetrahydrobenz[d]azepin-2-one intermediate which is useful as an intermediate of therapeutic agents for Alzheimer's disease.

X represents an ethylene group, an ethenylene group, or an arylene group, which may have a plurality of substituent groups. According to the first aspect of the present invention, X represents an ethylene group or an ethenylene group. According to the second aspect of the present invention, X represents an arylene group. Examples in which X represents an ethylene group are described in Reference Examples A1 to A4 and Examples A1 to A7 of the present specification. Examples in which X represents an arylene group are described in Reference Examples B1 to B3 and Examples B1 and B2 of the present specification. The type of the above substituent group is not particularly limited. Specific examples thereof include: halogen atoms such as fluorine, chlorine, and bromine; linear, cyclic, or branched alkyl groups such as a methyl group, an ethyl group, a cyclohexyl group, and an isopropyl group; aryl groups such as a phenyl group and a piperonyl group; heteroaryl groups such as a pyridyl group and a thienyl group; alkoxy groups such as a methoxy group, an ethoxy group, and an isopropoxy group; aryloxy groups such as a phenoxy group and a naphthyloxy group; carbonyl groups such as an acetyl group, an ethoxycarbonyl group, and a carbamoyl group; a cyano group; and a nitro group. Moreover, substituent groups may unitedly form a ring structure. Specific examples of the substituent groups which form a ring structure include a methylenedioxy group, an ethylenedioxy group, a carbonyldioxy group, an ureylene group, a trimethylene group, a tetramethylene group, fused benzene rings, fused furan rings, and fused imidazole rings.

In cases where X represents an ethylene group or an ethenylene group, preferred specific examples of X include an ethylene group, a 1,1-dimethoxyethylene group, an ethoxycarbonylethylene group, a carbamoylethylene group, a 1,2-cyclohexylene group, an ethenylene group, a 1,2-dimethylethenylene group, and an ethoxycarbonylethenylene group. In cases where X represents an arylene group, preferred specific examples of X include an imidazole-4,5-diyl group, an o-phenylene group, and a 4-fluoro-o-phenylene group. More preferred are an ethylene group, an ethenylene group, and an o-phenylene group which do not have a substituent group. Particularly preferred is an ethylene group which allows derivatization into an optically active 1-amino-3-methyl-1,3,4,5-tetrahydrobenz[d]azepin-2-one which is useful as an intermediate of therapeutic agents for Alzheimer's disease.

Specific examples of the isoquinoline derivative represented by the above formula (1) include ethyl 3,4-dihydroisoquinoline-1-carboxylate, methyl 3,4-dihydroisoquinoline-1-carboxylate, ethyl 3,4-dihydro-6-fluoroisoquinoline-1-carboxylate, ethyl isoquinoline-1-carboxylate, ethyl phenanthridine-6-carboxylate, 1-ethoxycarbonyl-2-methyl-3,4-dihydroisoquinolinium monomethylsulfate, 1-ethoxycarbonyl-2-methyl-3,4-dihydroisoquinolinium iodide, 1-ethoxycarbonyl-2-ethyl-3,4-dihydroisoquinolinium monoethylsulfate, 1-ethoxycarbonyl-2-ethyl-3,4-dihydroisoquinolinium iodide, 1-ethoxycarbonyl-2-phenyl-3,4-dihydroisoquinolinium iodide, 1-ethoxycarbonyl-2-benzyl-3,4-dihydroisoquinolinium bromide, 1-methoxycarbonyl-2-methyl-3,4-dihydroisoquinolinium monomethylsulfate, 1-phenoxylcarbonyl-2-methyl-3,4-dihydroisoquinolinium monomethylsulfate, 1-ethylthiocarbonyl-2-methyl-3,4-dihydroisoquinolinium monomethylsulfate, 1-phenylthiocarbonyl-2-methyl-3,4-dihydroisoquinolinium monomethylsulfate, 1-carbamoyl-2-methyl-3,4-dihydroisoquinolinium monomethylsulfate, 1-ethoxycarbonyl-6-fluoro-2-methyl-3,4-dihydroisoquinolinium monomethylsulfate, 1-ethoxycarbonyl-2-methylisoquinolinium monomethylsulfate, 6-ethoxycarbonyl-5-methylphenanthridinium monomethylsulfate, 6-ethoxycarbonyl-5-methylphenanthridinium iodide, 6-ethoxycarbonyl-5-(cyclopropylmethyl)phenanthridinium iodide, and 6-ethoxycarbonyl-5-(2,2,2-trifluoroethyl)phenanthridinium iodide.

Of the isoquinoline derivatives represented by the above formula (1), 3,4-dihydroisoquinolinium salts represented by the following formula (1a):

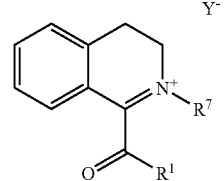

(1a)

wherein $R^1$, $R^7$, and $Y^-$ have the same definitions as described above;
are novel substances and useful intermediates in the production of benzazepinones which are useful as intermediates of pharmaceuticals and agrochemicals, and an optically active 1-amino-3-methyl-1,3,4,5-tetrahydrobenz[d]azepin-2-one which is useful as an intermediate of therapeutic agents for Alzheimer's disease.

The 3,4-dihydroisoquinolinium salts represented by the above formula (1a) are compounds in which the 1-position is substituted with a carbonyl group, and have a quaternary nitrogen atom at the 2-position and counter ion(s) $Y^-$.

In the above formula (1a), $R^1$ and $Y^-$ have the same definitions as described above; and $R^7$ represents a hydrogen atom, or an alkyl group or an aryl group containing 1 to 10 carbon atoms which may be substituted, and the alkyl group may take any of a linear form, a cyclic form, and a branched form. Specific examples of the alkyl group or the aryl group include, but not limited to: linear alkyl groups such as a methyl group, an ethyl group, a propyl group, and a butyl group; cyclic alkyl groups such as a cyclopentyl group and a cyclohexyl group; branched alkyl groups such as an isopropyl group, a 1-methylpropyl group, and a t-butyl group; aryl groups such as a phenyl group and a piperonyl group; and heteroaryl groups such as a pyridyl group and a thienyl group. Of these, preferred are linear alkyl groups that can be readily synthesized by using an alkylating agent. More preferred are a methyl group and an ethyl group that can be derivatized from dimethyl sulfate and diethyl sulfate of industrially inexpensive prices. Particularly preferred is a methyl group which allows derivatization into an optically active 1-amino-3-methyl-1,3,4,5-tetrahydrobenz[d]azepin-2-one which is useful as an intermediate of therapeutic agents for Alzheimer's disease. These groups may be arbitrarily substituted to the extent that the reaction of the present invention is not affected.

The type of the substituent group is not particularly limited. Specific examples thereof include: halogen atoms such as fluorine, chlorine, and bromine; linear, cyclic, or branched alkyl groups such as a methyl group, an ethyl group, a cyclopropyl group, a cyclohexyl group, and an isopropyl group; aryl groups such as a phenyl group and a piperonyl group; heteroaryl groups such as a pyridyl group and a thienyl group; alkoxy groups such as a methoxy group, an ethoxy group, and an isopropoxy group; a cyano group; and a nitro group. Preferred specific examples of the substituent group of the quaternary nitrogen atom having a substituent group include a trifluoromethyl group, a 2,2,2-trifluoroethyl group, a cyclopropylmethyl group, a benzyl group, a 2-(4-methoxyphenyl) ethyl group, and a 3-chlorophenyl group.

Specific examples of the 2-methyl-3,4-dihydroisoquinolinium salts represented by the above formula (1a) include 1-ethoxycarbonyl-2-methyl-3,4-dihydroisoquinolinium monomethylsulfate, 1-ethoxycarbonyl-2-methyl-3,4-dihydroisoquinolinium iodide, 1-ethoxycarbonyl-2-ethyl-3,4-dihydroisoquinolinium monoethylsulfate, 1-ethoxycarbonyl-2-ethyl-3,4-dihydroisoquinolinium iodide, 1-ethoxycarbonyl-2-phenyl-3,4-dihydroisoquinolinium iodide, 1-ethoxycarbonyl-2-benzyl-3,4-dihydroisoquinolinium bromide, 1-methoxycarbonyl-2-methyl-3,4-dihydroisoquinolinium monomethylsulfate, 1-phenoxylcarbonyl-2-methyl-3,4-dihydroisoquinolinium monomethylsulfate, 1-ethylthiocarbonyl-2-methyl-3,4-dihydroisoquinolinium monomethylsulfate, 1-phenylthiocarbonyl-2-methyl-3,4-dihydroisoquinolinium monomethylsulfate, and 1-carbamoyl-2-methyl-3,4-dihydroisoquinolinium monomethylsulfate.

The benzazepinones represented by the above formula (2) are benz[d]azepin-2-ones in which the 1-position is substituted with an imino group, including 7-iminodibenz[b,d] azepin-6-ones in which the azepinone ring is substituted with an aromatic ring. In the benzazepinone represented by the above formula (2), the imino group may form a salt such as hydrochloride, sulfate, acetate, and oxalate. In cases where the imino group is a hydroxyimino group, it may form a salt in which the hydrogen atom in the hydroxyimino group is substituted with sodium, potassium, lithium, magnesium, or the like.

In the above formula (2), $R^2$ to $R^5$, $R^7$, and X have the same definitions as described above; and $R^6$ represents a hydrogen atom, a hydroxyl group, an alkoxy group, an aryloxy group, an amino group, or an alkyl group or an aryl group containing 1 to 10 carbon atoms, and may have a substituent group.

Specific examples of the alkoxy group include, but not limited to: linear alkoxy groups such as a methoxy group, an ethoxy group, a propoxy group, and a butoxy group; cyclic alkoxy groups such as a cyclopentyloxy group and a cyclohexyloxy group; branched alkoxy groups such as an isopropoxy group, a 1-methylpropyloxy group, and a t-butoxy group; and substituted alkoxy groups such as a benzyloxy group and a 2-chloroethoxy group.

Specific examples of the aryloxy group include, but not limited to: a phenoxy group; and substituted aryloxy groups such as a 4-methoxyphenoxy group, a pentafluorophenoxy group, and a 2-nitrophenoxy group.

Specific examples of the amino group include, but not limited to: an unsubstituted amino group; primary amino groups such as a methylamino group, an ethylamino group, an isopropylamino group, a cyclohexylamino group, and an anilino group; secondary amino groups such as a dimethylamino group, a diethylamino group, a diisopropylamino group, a methylpropylamino group, and a dicyclohexylamino group; substituted alkylamino groups such as a benzylamino group and a 2-cyanoethylamino group; substituted arylamino groups such as a 4-methoxyphenylamino group and a 4-chlorophenylamino group; and cyclic amino groups such as a piperidino group and a morpholino group.

Specific examples of the alkyl group or the aryl group include, but not limited to: linear alkyl groups such as a methyl group, an ethyl group, a propyl group, and a butyl group; cyclic alkyl groups such as a cyclopentyl group and a cyclohexyl group; branched alkyl groups such as an isopropyl group, a 1-methylpropyl group, and a t-butyl group; aryl groups such as a phenyl group and a piperonyl group; and heteroaryl groups such as a pyridyl group and a thienyl group. These groups may be arbitrarily substituted to the extent that the reaction of the present invention is not affected. The type of the substituent group is not particularly limited. Specific examples thereof include: halogen atoms such as fluorine, chlorine, and bromine; linear, cyclic, or branched alkyl groups such as a methyl group, an ethyl group, a cyclohexyl group, and an isopropyl group; aryl groups such as a phenyl group and a piperonyl group; heteroaryl groups such as a pyridyl group and a thienyl group; alkoxy groups such as a methoxy group, an ethoxy group, a phenoxy group, and an isopropoxy group; a cyano group; and a nitro group.

Of these, preferred are: a hydroxyl group prepared from alkoxyamine which can be produced under acidic conditions; alkoxy groups such as a methoxy group, an ethoxy group, and a benzyloxy group; and aryloxy groups such as a phenoxy group and a 4-methoxyphenoxy group. More preferred is a hydroxyl group that can be synthesized from inexpensive hydroxylamine.

Specific examples of the benzazepinones represented by the above formula (2) include 1-(hydroxyimino)-3-methyl-1,3,4,5-tetrahydrobenz[d]azepin-2-one, 1-(methoxyimino)-3-methyl-1,3,4,5-tetrahydrobenz[d]azepin-2-one, 3-methyl-1-(methylhydrazono)-1,3,4,5-tetrahydrobenz[d]azepin-2-one, 3-methyl-1-imino-1,3,4,5-tetrahydrobenz[d]azepin-2-one, 3-methyl-1-(methylimino)-1,3,4,5-tetrahydrobenz[d]azepin-2-one, 3-methyl-1-(benzylimino)-1,3,4,5-tetrahydrobenz[d]azepin-2-one, 1-(hydroxyimino)-3-methyl-1,3,4,5-tetrahydrobenz[d]azepin-2-one sodium salt, 7-fluoro-1-(hydroxyimino)-3-methyl-1,3,4,5-tetrahydrobenz[d]azepin-2-one, 1-(hydroxyimino)-3-methyl-1,3-dihydrobenz[d]azepin-2-one, 1-(hydroxyimino)-1,3,4,5-tetrahydrobenz[d]azepin-2-one, 3-ethyl-1-(hydroxyimino)-1,3,4,5-tetrahydrobenz[d]azepin-2-one, 1-(hydroxyimino)-3-phenyl-1,3,4,5-tetrahydrobenz[d]azepin-2-one, 3-benzyl-1-(hydroxyimino)-1,3,4,5-tetrahydrobenz[d]azepin-2-one, 7-(hydroxyimino)-5-methyl-5,7-dihydrodibenz[b,d]azepin-6-one, 7-(methoxyimino)-5-methyl-5,7-dihydrodibenz[b,d]azepin-6-one, 7-(hydroxyimino)-5-methyl-5,7-dihydrodibenz[b,d]azepin-6-one sodium salt, 7-(hydroxyimino)-5,7-dihydrodibenz[b,d]azepin-6-one, 5-(cyclopropylmethyl)-7-

(hydroxyimino)-5,7-dihydrodibenz[b,d]azepin-6-one, and 7-(hydroxyimino)-5-(2,2,2-trifluoroethyl)-5,7-dihydrodibenz[b,d]azepin-6-one.

The isoquinoline derivatives represented by the above formula (1) can be arbitrarily produced by publicly known methods (for example, Mendeleev Commun., 1996, 239). In particular, isoquinolinium salts, 3,4-dihydroisoquinolinium salts, and phenanthridinium salts in which the nitrogen atom at the 2-position has a substituent group can be produced by reacting isoquinolines, 3,4-dihydroisoquinolines, and phenanthridines in which the nitrogen atom at the 2-position does not have a substituent group, with an alkylating agent such as alkyl halide and dialkyl sulfate. At this time, such isoquinolinium salts, 3,4-dihydroisoquinolinium salts, and phenanthridinium salts may be isolated in the form of salt, although unpurified ones are preferably used for the reaction, from the viewpoint of simplification of the process.

The above invention includes two reactions of: a ring-opening reaction through cleavage of the carbon-nitrogen double bond in a six-membered ring fused to a benzene ring; and a ring-closing reaction by forming a seven-membered lactam ring using thus generated amine so as to convert into a benzazepinone. These two ring-opening and ring-closing reactions may include one or a plurality of other conversion reactions therebetween, although they are preferably performed in a consecutive manner since the number of steps can be reduced and simplified. Moreover, the two ring-opening and ring-closing reactions may be performed all at once under the same conditions, or the 1-position may also be converted into an imino group after the ring-closing reaction.

The above ring-opening reaction can be arbitrarily performed by publicly known methods which decompose imines and iminium salts. Specific examples thereof include, but not limited to: methods which treat with an amine such as methylamine, hydroxylamine, and benzyloxyamine, or a salt thereof, under an acidic or basic condition or under the presence of a catalyst, so as to form a ring-opened imine; methods which treat with water under an acidic condition or under the presence of a catalyst, so as to form a ketone; and methods which treat with an alcohol such as ethanol, diol such as ethyleneglycol, thiol such as ethanethiol, or dithiol such as 1,3-propanedithiol under an acidic condition or under the presence of a catalyst, so as to form acyclic or cyclic acetal or dithioacetal. Of these, preferred are methods which treat with an amine or a salt thereof, under an acidic or basic condition or under the presence of a catalyst, so as to form a ring-opened imine, and which allow conversion into benzazepinones represented by the above formula (2) through only two ring-opening and ring-closing reactions.

The above ring-closing reaction is a reaction to form a seven-membered lactam ring between an amine and a carboxylic acid derivative, and can be arbitrarily performed by publicly known methods such as heating in a solvent. Moreover, the reaction may be performed under the presence of a catalyst such as acid or base, if necessary. Furthermore, in cases where the ring-closing reaction is performed with a substrate which has produced ketone, acetal, or dithioacetal through the ring-opening reaction, the 1-position of the benzazepinone has to be converted into an imino group, which can be arbitrarily performed by publicly known methods. Specific examples thereof include, but not limited to methods which treat acetal or dithioacetal with water under an acidic condition or under the presence of a catalyst, to form a ketone, followed by treatment with an amine such as methylamine, hydroxylamine, and benzyloxyamine, or a salt thereof, under an acidic or basic condition or under the presence of a catalyst, so as to convert into an imino group.

Specific examples of the intermediates mediating the above reaction include, but not limited to: carboxylic acid derivatives having an imino group at the 2-position such as ethyl hydroxyimino-[2-(2-methylaminoethyl)phenyl]acetate, ethyl benzylimino-[2-(2-methylaminoethyl)phenyl]acetate, and ethyl hydroxyimino-(2'-methylaminobiphenyl-2-yl)acetate; carboxylic acid derivatives having a ketone group at the 2-position such as ethyl[2-(2-methylaminoethyl)phenyl]-oxoacetate and ethyl (2'-methylaminobiphenyl-2-yl)-oxoacetate; carboxylic acid derivatives having an acetal group at the 2-position such as ethyl diethoxy-[2-(2-methylaminoethyl)phenyl]acetate, ethyl 2-[2-(2-methylaminoethyl)phenyl]-1,3-dioxolane-2-carboxylate, and ethyl 2-(2'-methylaminobiphenyl-2-yl)-1,3-dioxolane-2-carboxylate; and carboxylic acid derivatives having dithioacetal at the 2-position such as ethyl diethylthio-[2-(2-methylaminoethyl)phenyl]acetate, ethyl 2-[2-(2-methylaminoethyl)phenyl]-1,3-dithiane-2-carboxylate, and ethyl diethylthio-(2'-methylaminobiphenyl-2-yl)acetate. Of these, preferred are carboxylic acid derivatives having an imino group at the 2-position which are represented by the following formula (3):

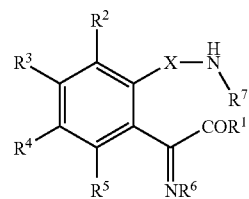

wherein $R^1$ to $R^7$ and X have the same definitions as described above, which can be immediately converted into benzazepinones represented by the above formula (2) through ring-closing reaction.

The 2-iminocarboxylic acid derivatives represented by the above formula (3) are acetic acid derivatives in which the 2-position is substituted with an imino group and an aromatic ring, and are compounds in which the ortho position of the aromatic ring has a linker of two carbon length and an amino group. In the above formula (3), $R^1$, $R^2$ to $R^7$, and X have the same definitions as described above. In the 2-iminocarboxylic acid derivative represented by the above formula (3), the amino group and/or imino group may form a salt such as hydrochloride, sulfate, acetate, and oxalate. In cases where the imino group is a hydroxyimino group, it may form a salt in which the hydrogen atom in the hydroxyimino group is substituted with sodium, potassium, lithium, magnesium, or the like.

The 2-iminocarboxylic acid derivatives represented by the above formula (3) are novel compounds and useful intermediates in the production of benzazepinones represented by the above formula (2), and an optically active 1-amino-3-methyl-1,3,4,5-tetrahydrobenz[d]azepin-2-one which is useful as an intermediate of therapeutic agents for Alzheimer's disease.

Specific examples of the 2-iminocarboxylic acid derivatives represented by the above formula (3) include ethyl hydroxyimino-[2-(2-methylaminoethyl)phenyl]acetate, ethyl methoxyimino-[2-(2-methylaminoethyl)phenyl]acetate, ethyl[2-(2-methylaminoethyl)phenyl]-methylhydrazonoacetate, ethyl imino-[2-(2-methylaminoethyl)phenyl]acetate, ethyl[2-(2-methylaminoethyl)phenyl]-methyliminoacetate, ethyl benzylimino-[2-(2-methylaminoethyl)phenyl]acetate, hydrochloride salt of ethyl hydroxyimino-[2-(2-methylaminoethyl)phenyl]acetate, sulfate salt of ethyl hydroxyimino-[2-(2-methylaminoethyl)phenyl]acetate, sodium salt of ethyl hydroxyimino-[2-(2-methylaminoethyl)phenyl]acetate, ethyl hydroxyimino-[4-fluoro-2-(2-methylaminoethyl)phenyl]acetate, ethyl hydroxyimino-[2-(2-methylaminovinyl)phenyl]acetate, ethyl (2-aminoethylphenyl)-hydroxyiminoacetate, ethyl[2-(2-ethylaminoethyl)phenyl]-hydroxyiminoacetate, ethyl hydroxyimino-[2-(2-phenylaminoethyl)phenyl]acetate, ethyl[2-(2-benzylaminoethyl)phenyl]-hydroxyiminoacetate, ethyl hydroxyimino-(2'-methylaminobiphenyl-2-yl)acetate, ethyl methoxyimino-(2'-methylaminobiphenyl-2-yl)acetate, hydrochloride salt of ethyl hydroxyimino-(2'-methylaminobiphenyl-2-yl)acetate, sulfate salt of ethyl hydroxyimino-(2'-methylaminobiphenyl-2-yl)acetate, sodium salt of ethyl hydroxyimino-(2'-methylaminobiphenyl-2-yl)acetate, ethyl (2'-aminobiphenyl-2-yl)-hydroxyiminoacetate, ethyl[2'-(cyclopropylmethyl)aminobiphenyl-2-yl]-hydroxyiminoacetate, and ethyl hydroxyimino-[2'-(2,2,2-trifluoroethyl)aminobiphenyl-2-yl]acetate.

The 2-iminocarboxylic acid derivatives represented by the above formula (3) can be produced by reacting isoquinoline derivatives represented by the above formula (1) with an amine or a salt thereof by the method of the present invention.

The isoquinoline derivatives represented by the above formula (1) can be arbitrarily produced by publicly known methods. Moreover, isoquinolinium salts, 3,4-dihydroisoquinolinium salts, and phenanthridinium salts in which the nitrogen atom at the 2-position has a substituent group can be produced by reacting isoquinolines, 3,4-dihydroisoquinolines, and phenanthridines in which the nitrogen atom at the 2-position does not have a substituent group, with an alkylating agent such as alkyl halide and dialkyl sulfate. At this time, such isoquinolinium salts, 3,4-dihydroisoquinolinium salts, and phenanthridinium salts may be isolated in the form of salt, although unpurified ones are preferably used for the reaction with an amine or a salt thereof, from the viewpoint of simplification of the operation. In cases where unpurified ones are used for the reaction with an amine or a salt thereof, the solvent may be replaced by concentration, although the reaction is preferably performed not by concentrating the solvent, but by using the same solvent or adding an additional solvent, from the viewpoints of simplification and safety of the operation.

Examples of the amine or the salt thereof used for the above reaction include: ammonia; primary amines such as methylamine, ethylamine, benzylamine, 1-phenylethylamine, and aniline; hydroxylamine; alkoxyamines such as methoxyamine, ethoxyamine, and benzyloxyamine; aryloxyamines such as phenoxylamine and 4-methoxyphenoxylamine; hydrazines such as hydrazine, methylhydrazine, 1,1-dimethylhydrazine, and benzylhydrazine; hydrazides such as methylsulfonhydrazide and p-toluenesulfonhydrazide; and the salts thereof. Of these, preferred are: hydroxylamine; alkoxyamines such as methoxyamine, ethoxyamine, and benzyloxyamine; aryloxyamines such as phenoxylamine and 4-methoxyphenoxyamine; and the salts thereof, which are irreversibly reactable under acidic conditions. More preferred are inexpensive hydroxylamine and the salts thereof, and particularly preferred are easily-handled and inexpensive hydroxylamine hydrochloride and hydroxylamine sulfate, which are acidic salts to thereby function as acid catalysts. Moreover, the dose of the amine or the salt thereof is 1 to 10 equivalents with respect to the isoquinoline derivative represented by the above formula (1), preferably 1 to 3 equivalents, and more preferably 1.0 to 1.5 equivalents.

The above reaction is preferably performed without addition of any additive from the viewpoint of cost saving, although additive(s) which accelerate the reaction may be added, if necessary. The additive is not particularly limited and publicly known ones can be used. Examples thereof include: inorganic acids such as hydrochloric acid, sulfuric acid, and perchloric acid; organic acids such as acetic acid, trifluoroacetic acid, tosyl acid; inorganic bases such as sodium hydroxide, lithium hydroxide, and sodium carbonate; and organic bases such as pyridine, triethylamine, and 1,8-diazabicyclo[5.4.0]undec-7-ene. A plurality of additives selected therefrom may be used in mixture at arbitrary ratios. Moreover, the dose of the additive is 0.001 to 10 equivalents with respect to the isoquinoline derivative represented by the above formula (1), preferably 0.01 to 1 equivalents, and more preferably 0.1 to 0.5 equivalents.

The above reaction can be performed without using a solvent, although a solvent is preferably used from the viewpoint of safety of the operation. The solvent to be used is not particularly limited unless the reaction is negatively affected. Specific examples thereof include: hexane, heptane, benzene, toluene, and other hydrocarbon-based solvents; ethylether, propylether, cyclopentylmethylether, t-butylmethylether, tetrahydrofuran, and other ether-based solvents; dichloromethane, chloroform, dichloroethane, chlorobenzene, and other halogen-based solvents; ethyl acetate, butyl acetate, and other ester-based solvents; acetone, methylethylketone, and other ketone-based solvents; dimethylformamide, N-methylpyrrolidone, and other amide-based solvents; dimethyl carbonate, diethyl carbonate, and other carboxylate ester-based solvents; acetonitrile and other nitrile-based solvents; methanol, ethanol, 2-propanol, and other alcohol-based solvents; and water. The amines and the salts thereof may also be used as solvent. A plurality of solvents selected therefrom may be used in mixture at arbitrary ratios. Generally preferred solvents include ether-based solvents, nitrile-based solvents, and alcohol-based solvents, and more preferred include tetrahydrofuran, acetonitrile, methanol, and ethanol. The preferred solvent depends on the condition of amine or the like to be used. In cases where hydroxylamine hydrochloride or hydroxylamine sulfate serving as particularly preferred amine, is used, preferred are highly polar alcohol-based solvents, water, and mixed solvent system containing such solvent(s) and arbitrary solvent(s), so as to dissolve the salt. More preferred are water and mixed solvent system containing water and arbitrary solvent(s). Moreover, regarding the dose of the solvent, such solvent may be used at any amount, although the amount is normally 0.5 to 50-fold volume with respect to the isoquinoline derivative represented by the above formula (1), preferably 1 to 10-fold volume, and more preferably 1 to 3-fold volume.

The reaction temperature is not particularly limited to the extent that the reaction is not negatively affected, and is normally −20° C. to 120° C., preferably 0° C. to 70° C., and more preferably 20° C. to 50° C.

The reaction time of the above reaction is not particularly limited to the extent that the reaction is not negatively affected, although the reaction is preferably performed within a range of 10 minutes to 24 hours from the viewpoint of saving the production cost, and more preferably within 1 hour to 10 hours.

The 2-iminocarboxylic acid derivative represented by the above formula (3) obtained through the above reaction can be used in the next step without purification, although it is preferably purified by some means such as extraction and/or crystallization.

The solvent to be used for such extraction and/or crystallization is not particularly limited. Specific examples thereof include: hexane, heptane, benzene, toluene, and other hydrocarbon-based solvents; ethylether, propylether, cyclopentylmethylether, t-butylmethylether, tetrahydrofuran, and other ether-based solvents; dichloromethane, chloroform, dichloroethane, chlorobenzene, and other halogen-based solvents; ethyl acetate, butyl acetate, and other ester-based solvents; acetone, methylethylketone, and other ketone-based solvents; dimethyl carbonate, diethyl carbonate, and other carboxylate ester based solvents; acetonitrile and other nitrile-based solvents; methanol, ethanol, 2-propanol, and other alcohol-based solvents; and water. A plurality of solvents selected therefrom may be used in mixture at arbitrary ratios. The crystallization is preferably performed with the original reaction solvent or by adding another solvent from the viewpoints of simplification of the operation and saving the amount of solvent to be used. More preferred solvents for crystallization include hexane, heptane, toluene, ethyl acetate, acetone, acetonitrile, methanol, ethanol, water, and mixed solvents thereof, and particularly preferred are mixed solvents of organic solvents which dissolve organic substances in impurities and water which dissolves salts.

Moreover, it is also preferable to add an acid or base during the crystallization so as to lower the solubility of the 2-iminocarboxylic acid derivative represented by the formula (3). In cases where hydroxylamine hydrochloride or hydroxylamine sulfate serving as particularly preferred amine or the salt thereof, is used, the reaction system becomes acidic, and therefore it is preferable to add a base to neutralize the amine since the solubility is lowered and the crystallization becomes more efficient.

Here, the term crystallization includes normal crystallization in which a poor solvent, an acid, a base, or the like is added to a solution to lower the solubility so as to obtain a substance of interest in the form of crystals, as well as recrystallization in which once obtained crude crystals or the like are dissolved in an appropriate solvent and then are recrystallized.

The 2-iminocarboxylic acid derivatives represented by the above formula (3) can be converted into benzazepinones represented by the above formula (2) through lactamization by the method of the present invention.

The above reaction proceeds without addition of any additive, although additive(s) which accelerate the reaction are preferably added. The additive is not particularly limited. Specific examples thereof include: inorganic bases such as sodium hydroxide, lithium hydroxide, and sodium carbonate; metal alkoxides such as sodium methoxide, sodium ethoxide, and potassium ethoxide; and organic bases such as pyridine, triethylamine, and 1,8-diazabicyclo[5.4.0]undec-7-ene. A plurality of additives selected therefrom may be used in mixture at arbitrary ratios. Of these, preferred are metal alkoxides or organic bases which do not generate water as a by-product which causes hydrolysis of the 2-iminocarboxylic acid derivative represented by the above formula (3), and more preferred are metal alkoxides which generate alcohol as a by-product which can be readily removed by purification, and inexpensive. Moreover, the dose of the additive is 0.1 to 10 equivalents with respect to the 2-iminocarboxylic acid derivative represented by the above formula (3), preferably 0.1 to 2 equivalents, and more preferably 0.5 to 1 equivalents.

In the above reaction, a solvent is preferably used. The solvent to be used is not particularly limited unless the reaction is negatively affected. Specific examples thereof include: hexane, heptane, benzene, toluene, and other hydrocarbon-based solvents; ethylether, propylether, cyclopentylmethylether, t-butylmethylether, tetrahydrofuran, and other ether-based solvents; dichloromethane, chloroform, dichloroethane, chlorobenzene, and other halogen-based solvents; acetone, methylethylketone, and other ketone-based solvents; dimethylformamide, N-methylpyrrolidone, and other amide-based solvents; acetonitrile and other nitrile-based solvents; methanol, ethanol, 2-propanol, and other alcohol-based solvents; and water. Additives may also be used as solvent. A plurality of solvents selected therefrom may be used in mixture at arbitrary ratios. Preferred solvents are highly polar alcohol-based solvents, and mixed solvent system containing such solvent(s) and arbitrary solvent(s). More preferred is sole use of an alcohol-based solvent. Particularly preferred are inexpensive methanol and ethanol. Moreover, regarding the dose of the solvent, such solvent may be used at any amount, although the amount is normally 1 to 50-fold volume with respect to the 2-iminocarboxylic acid derivative represented by the above formula (3), and preferably 2 to 10-fold volume.

The reaction temperature is not particularly limited to the extent that the reaction is not negatively affected, and is normally −20° C. to 120° C., preferably 20° C. to 100° C., and more preferably 40° C. to 70° C.

The reaction time of the above reaction is not particularly limited to the extent that the reaction is not negatively affected, although the reaction is preferably performed within a range of 10 minutes to 24 hours from the viewpoint of saving the production cost, and more preferably within 1 hour to 10 hours.

The benzazepinones represented by the above formula (2) obtained through the above reaction can be purified by some means such as extraction and/or crystallization, although unpurified ones are preferably used for next steps to simplify the operation. In cases where unpurified ones are used for next steps, the solvent may be replaced by concentration, although the reaction is preferably performed not by concentrating the solvent, but by using the same solvent or adding an additional solvent, from the viewpoints of simplification and safety of the operation.

<Method for Producing Optically Active Aminobenzazepinone>

Benzazepinones represented by the above formula (2) produced by the present invention are useful as intermediates of various pharmaceuticals and agrochemicals. In particular, optically active aminobenzazepinones represented by the following formula (5):

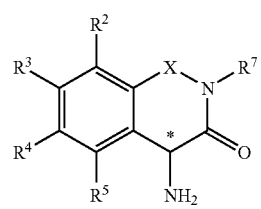

(5)

wherein $R^2$ to $R^5$, $R^7$, and X have the same definitions as described above;
are industrially useful as intermediates of therapeutic agents for Alzheimer's disease (for example, PCT International Publication No. WO 2002/47671). The conversion into optically active aminobenzazepinones represented by the above formula can be achieved by reducing benzazepinones represented by the above formula (2) to thereby form aminobenzazepinones represented by the following formula (4):

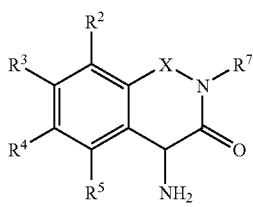

(4)

wherein $R^2$ to $R^5$, $R^7$, and X have the same definitions as described above, and by subsequently using a method such as resolution.

Specific examples of the aminobenzazepinones represented by the above formula (5) include: in those cases where X represents an ethylene group or an ethenylene group, (S)-1-amino-3-methyl-1,3,4,5-tetrahydrobenz[d]azepin-2-one, (R)-1-amino-3-methyl-1,3,4,5-tetrahydrobenz[d]azepin-2-one, (S)-1-amino-7-fluoro-3-methyl-1,3,4,5-tetrahydrobenz[d]azepin-2-one, (R)-1-amino-7-fluoro-3-methyl-1,3,4,5-tetrahydrobenz[d]azepin-2-one, (S)-1-amino-3-ethyl-1,3,4,5-tetrahydrobenz[d]azepin-2-one, (R)-1-amino-3-ethyl-1,3,4,5-tetrahydrobenz[d]azepin-2-one, (S)-1-amino-3-phenyl-1,3,4,5-tetrahydrobenz[d]azepin-2-one, (R)-1-amino-3-phenyl-1,3,4,5-tetrahydrobenz[d]azepin-2-one, (S)-1-amino-3-benzyl-1,3,4,5-tetrahydrobenz[d]azepin-2-one, (R)-1-amino-3-benzyl-1,3,4,5-tetrahydrobenz[d]azepin-2-one, (S)-1-amino-3-methyl-1,3-dihydrobenz[d]azepin-2-one, (R)-1-amino-3-methyl-1,3-dihydrobenz[d]azepin-2-one, (S)-1-amino-1,3,4,5-tetrahydrobenz[d]azepin-2-one, and (R)-1-amino-1,3,4,5-tetrahydrobenz[d]azepin-2-one; and, in those cases where X represents an arylene group, (S)-7-amino-5-methyl-5,7-dihydrodibenz[b,d]azepin-6-one, (R)-7-amino-5-methyl-5,7-dihydrodibenz[b,d]azepin-6-one, (S)-7-amino-5,7-dihydrodibenz[b,d]azepin-6-one, (R)-7-amino-5,7-dihydrodibenz[b,d]azepin-6-one, (S)-7-amino-5-cyclopropylmethyl-5,7-dihydrodibenz[b,d]azepin-6-one, (R)-7-amino-5-cyclopropylmethyl-5,7-dihydrodibenz[b,d]azepin-6-one, (S)-7-amino-5-(2,2,2-trifluoroethyl)-5,7-dihydrodibenz[b,d]azepin-6-one, and (R)-7-amino-5-(2,2,2-trifluoroethyl)-5,7-dihydrodibenz[b,d]azepin-6-one.

Specific examples of the aminobenzazepinones represented by the above formula (4) include: in those cases where X represents an ethylene group or an ethenylene group, 1-amino-3-methyl-1,3,4,5-tetrahydrobenz[d]azepin-2-one, 1-amino-7-fluoro-3-methyl-1,3,4,5-tetrahydrobenz[d]azepin-2-one, 1-amino-3-ethyl-1,3,4,5-tetrahydrobenz[d]azepin-2-one, 1-amino-3-phenyl-1,3,4,5-tetrahydrobenz[d]azepin-2-one, 1-amino-3-benzyl-1,3,4,5-tetrahydrobenz[d]azepin-2-one, 1-amino-3-methyl-1,3-dihydrobenz[d]azepin-2-one, and 1-amino-1,3,4,5-tetrahydrobenz[d]azepin-2-one; and, in those cases where X represents an arylene group, 7-amino-5-methyl-5,7-dihydrodibenz[b,d]azepin-6-one, 7-amino-5,7-dihydrodibenz[b,d]azepin-6-one, 7-amino-5-cyclopropylmethyl-5,7-dihydrodibenz[b,d]azepin-6-one, and 7-amino-5-(2,2,2-trifluoroethyl)-5,7-dihydrodibenz[b,d]azepin-6-one.

The above aminobenzazepinones represented by the formula (5) and formula (4) can be present in the form of corresponding salt.

Among the above reactions, reduction reaction can be arbitrarily performed by publicly known methods. Examples thereof include: hydrogenation reactions using a heavy metal catalyst such as palladium carbon and Raney nickel; reactions using a hydride reducing agent such as sodium borohydride; reduction reactions using a combination of a hydride reducing agent and a heavy metal such as sodium borohydride and nickel chloride, and sodium borohydride and titanium tetrachloride; and reduction reactions using a single metal such as zinc and sodium.

Moreover, among the above reactions, resolution can be performed by methods using an optically active acid as a resolving agent, according to publicly known methods (for example, PCT International Publication No. WO 2002/40451 and Tetrahedron Asymmetry, 2005, 16, 3814). Here, the term resolution includes normal optical resolution which resolves racemates into R-form and S-form, as well as dynamic kinetic resolution which selectively obtains only one isomer while inducing racemization in the reaction system, and diastereomeric resolution of compounds having a plurality of asymmetric points. Moreover, in addition to resolution by means of an optically active salt using an optically active carboxylic acid, methods which treat with microbial forms and/or processed products of such microbial forms, such as asymmetric acylation reaction may also be included.

EXAMPLES

The present invention is hereafter described in greater detail with reference to the following examples, although the technical scope of the present invention is not limited thereto.

Reference Example A1

Preparation of Ethyl N-(2-phenylethyl)oxamate 181 g (1.24 mol) of diethyl oxalate and 500 ml of toluene were placed in a flask, to which 100 g (825 mmol) of 2-phenethylamine was added dropwise at room temperature for 45 minutes. The reaction mixture was heated at 60° C. for two hours, and was further reacted at 75° C. for two hours. The solution was then concentrated at room temperature until the residual quantity of toluene became about 50 ml. The generated precipitation was filtered off and washed with about 50 ml of toluene. 400 ml of hexane was added to the filtrate at 50° C., so as to precipitate crystals. The mixture was further cooled down to 5° C. and stirred for 30 minutes. Then, resulting crystals were filtered, washed with hexane, and dried to obtain 158 g (710 mmol, yield 86%) of ethyl N-(2-phenylethyl)oxamate as white crystals.

$^1$H-NMR (400 MHz, CDCl$_3$) δ 1.37 (3H, t, J=7.2 Hz), 2.88 (2H, t, J=7.1 Hz), 3.61 (2H, q, J=7.0 Hz), 4.33 (2H, q, J=7.2 Hz), 7.12 (1H, brs), 7.17-7.28 (3H, m), 7.30-7.35 (2H, m).

Reference Example A2

Preparation of Ethyl 3,4-dihydroisoquinoline-1-carboxylate 50 g (226 mmol) of ethyl N-(2-phenylethyl)oxamate obtained by the method of Reference Example A1, 31.5 ml (339 mmol) of phosphorus oxychloride, and 15.4 g (113 mmol) of zinc chloride were placed in a flask, and heated to 90° C. After two hours reaction, 50 ml of toluene was added thereto at 60° C. The mixture was further cooled down to a room temperature, and 25 ml of ethanol was added. Further, 100 ml of water, 200 ml of aqueous sodium hydroxide solution (25%), and 100 ml of ethyl acetate were added. The mixture was filtered through a celite pad and washed with 150 ml of ethyl acetate. The organic layer was separated, and then the aqueous layer was re-extracted with 200 ml of ethyl acetate. The organic layers were combined, followed by drying with magnesium sulfate and concentration to obtain 44 g of crude ethyl 3,4-dihydroisoquinoline-1-carboxylate, which was used in the next step without purification.

$^1$H-NMR (400 MHz, CDCl$_3$) δ 1.43 (3H, t, J=7.2 Hz), 2.74-2.81 (2H, m), 3.87-3.93 (2H, m), 4.44 (2H, q, J=7.2 Hz), 7.19-7.23 (1H, m), 7.29-7.35 (1H, m), 7.38-7.43 (1H, m), 7.67-7.72 (1H, m).

Reference Example A3

Preparation of 1-ethoxycarbonyl-2-methyl-3,4-dihydroisoquinolinium Iodide 1.89 g of crude ethyl 3,4-dihydroisoquinoline-1-carboxylate obtained by the method of Reference Example A2 and 9.5 ml of tetrahydrofuran were placed in a flask, to which 1.2 ml (19 mmol) of methyl iodide was added dropwise at room temperature for 30 minutes. After three days reaction, the mixture was filtered. The resulting crystals were washed with tetrahydrofuran and dried to obtain 2.25 g (6.52 mmol, yield 70%) of 1-ethoxycarbonyl-3,4-dihydro-2-methylisoquinolinium iodide as yellow crystals.

$^1$H-NMR (400 MHz, CDCl$_3$) δ 1.52 (3H, t, J=7.2 Hz), 3.61 (2H, t, J=8.1 Hz), 4.13 (3H, s), 4.70 (2H, q, J=7.1 Hz), 4.70 (2H, t, J=8.1 Hz), 7.44-7.55 (3H, m), 7.77-7.85 (1H, m).

Example A1

Preparation of Ethyl hydroxyimino-[2-(2-methylaminoethyl)phenyl]acetate 1.00 g (2.90 mmol) of 1-ethoxycarbonyl-3,4-dihydro-2-methylisoquinolinium iodide obtained by the method of Reference Example A3, 211 mg (3.04 mmol) of hydroxylamine hydrochloride, 2 ml of ethanol, and 0.2 ml of water were placed in a flask, and reacted at room temperature overnight. 30 mg (0.43 mmol) of hydroxylamine hydrochloride was additionally added thereto, followed by eight hours reaction. Then, about 1 g of aqueous sodium hydroxide solution (25%) and 6 ml of water were added thereto and the pH was adjusted at 9 to 10 to yield precipitation. Then, the precipitation was filtered, washed with water, and dried to obtain 0.51 g (2.04 mmol, yield 70%) of ethyl hydroxyimino-[2-(2-methylaminoethyl)phenyl]acetate as white crystals.

$^1$H-NMR (400 MHz, CDCl$_3$) δ 1.29 (3H, t, J=7.2 Hz), 2.44 (3H, s), 2.76-2.83 (2H, m), 2.86-2.92 (2H, m), 4.29 (2H, q, J=7.1 Hz), 7.08-7.12 (1H, m), 7.24-7.31 (2H, m), 7.32-7.37 (1H, m).

Reference Example A4

Preparation of 1-ethoxycarbonyl-2-methyl-3,4-dihydroisoquinolinium monomethylsulfate 60 g of crude ethyl 3,4-dihydroisoquinoline-1-carboxylate obtained by the method of Reference Example A2 and 60 ml of ethanol were placed in a flask, to which 27.8 ml (293 mmol) of dimethyl sulfate was added dropwise at room temperature for 30 minutes. The reaction mixture was left standing overnight to obtain a solution of 1-ethoxycarbonyl-3,4-dihydro-2-methylisoquinolinium monomethylsulfate, which was directly used in the next step.

$^1$H-NMR (400 MHz, CDCl$_3$) δ 1.52 (3H, t, J=7.1 Hz), 3.51 (2H, t, J=7.8 Hz), 3.71 (3H, s), 4.02 (3H, s), 4.53 (2H, t, J=7.9 Hz), 4.68 (2H, q, J=7.1 Hz), 7.45-7.53 (3H, m), 7.75-7.83 (1H, m).

Example A2

Preparation of Ethyl hydroxyimino-[2-(2-methylaminoethyl)phenyl]acetate

The 1-ethoxycarbonyl-3,4-dihydro-2-methylisoquinolinium monomethylsulfate solution obtained by Reference Example A4 was added with 60 ml of water and 22.4 g (322 mmol) of hydroxylamine hydrochloride in a flask. The mixture was stirred at room temperature for six hours. The reaction mixture was added with 120 ml of ethyl acetate, and then the pH was adjusted at 9 to 10 with about 103 g of aqueous sodium hydroxide solution (25%) to yield precipitation. The solution was stirred at 5° C. for 30 minutes. Then, the precipitation was filtered, washed with ethyl acetate, and dried to obtain 42.2 g (169 mmol, yield 55%, 3 steps) of ethyl hydroxyimino-[2-(2-methylaminoethyl)phenyl]acetate as white crystals.

Example A3

Preparation of 1-(hydroxyimino)-3-methyl-1,3,4,5-tetrahydrobenz[d]azepin-2-one 3.11 g (12.5 mmol) of ethyl hydroxyimino-[2-(2-methylaminoethyl)phenyl]acetate obtained by the method of Example A2, 4.25 g (12.5 mmol) of sodium ethoxide-20% ethanol solution, and 9.3 ml of ethanol were added into a flask, and reacted at 50° C. for seven hours. The resultant mixture was cooled down to a room temperature, added with 0.72 ml of acetic acid, and concentrated. Thus generated solid was added with ethyl acetate and water, followed by stirring. The precipitation was filtered and washed to obtain 1.87 g (9.2 mmol, yield 72%) of 1-(hydroxyimino)-3-methyl-1,3,4,5-tetrahydrobenz[d]azepin-2-one as a light brown solid.

$^1$H-NMR (400 MHz, CDCl$_3$) δ 3.08 (3H, s), 3.10-3.16 (2H, m), 3.70-3.76 (2H, m), 7.20-7.29 (2H, m), 7.30-7.35 (1H, m), 7.74-7.78 (1H, m), 8.78 (1H, brs).

Example A4

Preparation of 1-amino-3-methyl-1,3,4,5-tetrahydrobenz[d]azepin-2-one 42.0 g (168 mmol) of ethyl hydroxyimino-[2-(2-methylaminoethyl)phenyl]acetate obtained by the method of Example A2, 57 g (168 mmol) of sodium ethoxide-20% ethanol solution, and 126 ml of ethanol were added into a flask, and reacted at 50° C. for five hours to obtain a solution of 1-(hydroxyimino)-3-methyl-1,3,4,5-tetrahydrobenz[d]azepin-2-one. The reaction mixture was concentrated and then was added with 420 ml of 1N hydrochloric acid and 8.9 g of 5% palladium carbon. The mixture was treated under a hydrogen atmosphere at room temperature for 8.5 hours. The reaction mixture was filtered through a celite pad and the filtrate was extracted with dichloromethane under an alkaline condition. The extraction was concentrated to obtain 27.6 g (145 mmol, yield 86%) of 1-amino-3-methyl-1,3,4,5-tetrahydrobenz[d]azepin-2-one as a white solid.

$^1$H-NMR (400 MHz, CDCl$_3$) δ 3.02 (3H, s), 3.15 (1H, ddd, J=16.8, 10.3, 5.8 Hz), 3.25 (1H, dt, J=16.8, 5.1 Hz), 3.36 (1H, dt, J=14.6, 5.8 Hz), 4.14 (1H, ddd, J=14.6, 10.1, 4.6 Hz), 5.25 (1H, s), 7.09-7.13 (1H, m), 7.17-7.22 (1H, m), 7.23-7.28 (1H, m), 7.68-7.72 (1H, m).

Example A5

Preparation of (S)-1-amino-3-methyl-1,3,4,5-tetrahydrobenz[d]azepin-2-one Hydrochloride 36.8 g (242 mmol) of D-mandelic acid and 254 ml of 2-propanol were added into a flask, and were dissolved at 45° C. To this solution, an isopropyl acetate solution (169 ml) containing 47.0 g (247 mmol) of 1-amino-3-methyl-1,3,4,5-tetrahydrobenz[d]azepin-2-one obtained by the method of Example A4 was added dropwise at 45° C., followed by stirring for three hours. The reaction mixture was added with 2.06 g (12.4 mmol) of 5-nitrosalicylaldehyde, followed by further stirring for 13 hours. The resultant mixture was cooled down to a room temperature. Then, resulting crystals were filtered off, and suspended in 423 ml of ethyl acetate, to which 34.3 ml of concentrated hydrochloric acid was added at 50° C., followed by stirring for three hours. The resultant mixture was cooled down to a room temperature. Then, crystals were filtered off, washed, and dried to obtain 43.6 g (192 mmol, yield 78%, 99% ee) of (S)-1-amino-3-methyl-1,3,4,5-tetrahydrobenz[d]azepin-2-one hydrochloride as white crystals.

$^1$H-NMR (400 MHz, DMSO-$d_6$) δ 2.96 (3H, s), 3.24-3.34 (1H, m), 3.42-3.55 (2H, m), 4.30-4.39 (1H, m), 5.98 (1H, s), 7.39-7.50 (4H, m), 9.01 (3H, s).

Example A6

Preparation of Ethyl hydroxyimino-[2-(2-aminoethyl)phenyl]acetate 10.4 g (51.2 mmol) of ethyl 3,4-dihydroisoquinoline-1-carboxylate obtained by the method of Reference Example A2, 3.92 g (56.4 mmol) of hydroxylamine hydrochloride, 10 ml of ethanol, and 10 ml of water were placed in a flask, and reacted at room temperature for seven hours. The reaction mixture was added with 9.0 g of aqueous sodium hydroxide solution (25%) and 2.5 g of sodium chloride. Then, extraction was repeatedly performed with ethyl acetate. The organic layer was dried and concentrated to obtain 9.15 g of ethyl hydroxyimino-[2-(2-aminoethyl)phenyl]acetate as a highly viscous oil, which was directly used in the next step.

$^1$H-NMR (400 MHz, CDCl$_3$) δ 1.27 (3H, t, J=7.1 Hz), 2.74 (2H, t, J=6.8 Hz), 3.04 (2H, t, J=6.8 Hz), 4.28 (2H, q, J=7.1 Hz), 7.06-7.11 (1H, m), 7.16-7.40 (3H, m).

Example A7

Preparation of 1-(hydroxyimino)-1,3,4,5-tetrahydrobenz[d]azepin-2-one 9.15 g of ethyl hydroxyimino-[2-(2-aminoethyl)phenyl]acetate obtained by the method of Example A6, 13.2 g (38.7 mmol) of sodium ethoxide-20% ethanol solution, and 27 ml of ethanol were added into a flask, and reacted at 50° C. for three hours. The resultant mixture was cooled down to a room temperature, and then was added with 33 ml of 1N hydrochloric acid. The thus generated precipitation under ice cooling was filtered and washed to obtain 3.30 g (17.4 mmol, yield 34%, 2 steps) of 1-(hydroxyimino)-1,3,4,5-tetrahydrobenz[d]azepin-2-one as a white solid.

$^1$H-NMR (400 MHz, CDCl$_3$) δ 3.24 (2H, t, J=5.5 Hz), 3.59-3.65 (2H, m), 7.46-7.53 (2H, m), 7.55-7.60 (1H, m), 7.74-7.78 (1H, m), 8.36 (1H, t, J=5.6 Hz), 11.84 (1H, s).

Reference Example B1

Preparation of Ethyl N-biphenyl-2-yloxamate 5.08 g (30 mmol) of 2-aminobiphenyl, 50 ml of ethyl acetate, and 3.1 g (30 mmol) of triethylamine were placed in a flask, to which 4.1 g (30 mmol) of ethyl chloroglyoxylate was added dropwise under ice cooling. The reaction mixture was stirred at room temperature for three hours, and then 50 ml of ethyl acetate was added thereto. The organic layer was washed with 30 ml of 1N hydrochloric acid and 30 ml of brine one by one, and then was dried with anhydrous sodium sulfate. The solvent was removed by evaporation to obtain 6.8 g (24 mmol, yield 85%) of ethyl N-biphenyl-2-yloxamate as colorless crystals.

$^1$H-NMR (400 MHz, CDCl$_3$) δ 1.35 (3H, t, J=8.0 Hz), 4.31 (2H, q, J=8.0 Hz), 7.23-7.55 (8H, m), 8.48 (1H, d, J=8.0 Hz), 9.10 (1H, s).

Reference Example B2

Preparation of Ethyl phenanthridine-6-carboxylate 8.00 g (29.7 mmol) of ethyl N-biphenyl-2-yloxamate obtained by the method of Reference Example B1, 13.7 g (89 mmol) of phosphorus oxychloride, and 2.03 g (14.9 mmol) of zinc chloride were placed in a flask, and heated to 120° C. After seven hours reaction, 150 ml of ethyl acetate was added thereto at room temperature, and the mixture was poured into 100 ml of ice water. 50 ml of 25% sodium hydroxide was added thereto, and the mixture was stirred, filtered through a celite pad, and washed with 50 ml of ethyl acetate. The organic layer was separated, and the aqueous layer was re-extracted with 100 ml of ethyl acetate. The organic layers were combined, followed by drying with anhydrous sodium sulfate and concentration to obtain 4.9 g (19.5 mmol, yield 65%) of crude ethyl phenanthridine-6-carboxylate.

$^1$H-NMR (400 MHz, CDCl$_3$) δ 1.54 (3H, t, J=8.0 Hz), 4.64 (2H, q, J=8.0 Hz), 7.72-7.92 (4H, m), 8.30-8.80 (4H, m).

Reference Example B3

Preparation of 6-ethoxycarbonyl-5-methylphenanthridinium Monomethylsulfate 5.0 g (20 mmol) of crude ethyl phenanthridine-6-carboxylate obtained by the method of Reference Example B2, 2.5 g (20 mmol) of dimethyl sulfate, and 30 ml of nitromethane were placed in a flask, and reacted by heating under reflux for two hours. Then, the resultant mixture was cooled down. The solvent was concentrated in vacuo to obtain crude 6-ethoxycarbonyl-5-methylphenanthridinium monomethylsulfate, which was directly used in the next step.

Example B1

Preparation of Ethyl hydroxyimino-(2'-methylamino-biphenyl-2-yl)acetate

The crude 6-ethoxycarbonyl-5-methylphenanthridinium monomethylsulfate obtained by the method of Reference Example B3, 1.54 g (22 mmol) of hydroxylamine hydrochloride, 1.8 g (22 mmol) of sodium acetate, 6 ml of water, and 6 ml of ethanol were added into a flask. The reaction mixture was left standing at room temperature overnight. The reaction mixture was added with 15 ml of ethyl acetate and 15 ml of water, and then the pH was adjusted at 8 to 9 with saturated aqueous sodium bicarbonate. The organic layer was separated, and the aqueous layer was re-extracted with 30 ml of ethyl acetate twice. The organic layers were combined, and were dried with anhydrous sodium sulfate. Then, the solvent was removed by evaporation to obtain about 5 g of crude ethyl hydroxyimino-(2'-methylaminobiphenyl-2-yl)acetate as a yellow oil, which was used in the next step without purification.

Example B2

Preparation of 7-(hydroxyimino)-5-methyl-5,7-dihydrodibenz[b,d]azepin-6-one

About 5 g of crude ethyl hydroxyimino-(2'-methylaminobiphenyl-2-yl)acetate obtained by the method of Example B1, 6.8 g (20 mmol) of sodium ethoxide-20% ethanol solution, and 15 ml of ethanol were added into a flask, and reacted by heating under reflux for two hours. The mixture was cooled down to a room temperature, then added with 1.1 ml of acetic acid, and concentrated. The resultant mixture was dissolved in 50 ml of ethyl acetate, and was washed with 10 ml of brine, followed by drying with anhydrous sodium sulfate, concentration, and purification with silica gel column chromatography to obtain 1.1 g (mixed isomers, about 85:15, 4.4 mmol, yield 21%, 3 steps) of 7-(hydroxyimino)-5-methyl-5, 7-dihydrodibenz[b,d]azepin-6-one as a pale yellow oil.

Major isomer: $^1$H-NMR (400 MHz, CDCl$_3$) δ 3.45 (3H, s), 7.26-7.65 (8H, m), 8.25 (1H, brs).

INDUSTRIAL APPLICABILITY

The present invention is an epochal production method which converts from readily-synthesizable isoquinoline derivatives of six-membered rings fused to benzene rings into benzazepinones which are compounds of seven-membered rings fused to benzene rings and are normally difficult to synthesize, by a combination of ring-opening reaction and ring-closing reaction, and is a versatile method which produces benzazepinones, for the synthesis of which there have been no practical and inexpensive methods so far. Moreover, according to the present invention, novel 2-iminocarboxylic acid derivatives and an efficient and industrially preferable production method thereof have been found; and further, a method for converting such derivatives into benzazepinones has been established. This has made it possible to produce benzazepinones and optically active aminobenzazepinones which are useful compounds as intermediates of pharmaceuticals and agrochemicals, under inexpensive and practical conditions. Benzazepinones produced by the method of the present invention can be derivatized into agents which are known to be useful as therapeutic agents for Alzheimer's disease, via an optically active 1-aminobenz[d]azepin-2-ones or the like, and thus are useful compounds as intermediates of pharmaceuticals or agrochemicals. Therefore, the present invention providing a practically suitable industrial production method thereof has a high utility value in terms of industry.

The invention claimed is:

1. A method for producing a benzazepinone represented by formula (2), or a salt thereof, which comprises:
opening a ring of an isoquinoline derivative represented by formula (1) by reaction of the isoquinoline derivative with an amine or a salt thereof; and subsequently converting the thus generated amine into a benzazepinone through a lactamization reaction by heating the amine in a solvent; wherein
formula (1) is

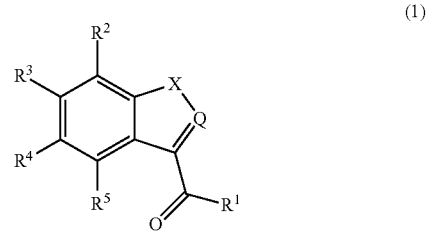

wherein $R^1$ represents an alkoxy group; each of $R^2$ to $R^5$ independently represents a hydrogen atom, an alkoxy group, or an alkyl group containing 1 to 10 carbon atoms; X represents an ethylene group or an arylene group; and Q is a tertiary or quaternary nitrogen atom, which, in those cases of a quaternary form, is substituted with an alkyl group or an aryl group containing 1 to 10 carbon atoms and has counter ion(s) $Y^-$, wherein $Y^-$ represents a halide ion, an inorganic acid ion, an alkylsulfate ion, a mesylate ion, a tosylate ion, an alkylsulfonate ion, an organic acid ion, and/or a hydroxide ion;
and formula (2) is

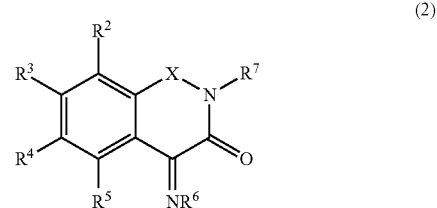

wherein $R^2$ to $R^5$ and X have the same definitions as described above; $R^6$ represents a hydrogen atom, a hydroxyl group, an alkoxy group, an aryloxy group, an amino group, or an alkyl group or an aryl group containing 1 to 10 carbon atoms; and $R^7$ represents a hydrogen atom or an alkyl group containing 1 to 10 carbon atoms.

2. A method for producing an aminobenzazepinone or a salt thereof, which comprises:
producing a benzazepinone represented by the formula (2) or a salt thereof through the method according to claim 1; and
reducing the benzazepinone represented by (2) or the salt thereof which has been produced in the above manner, to thereby convert into an aminobenzazepinone represented by formula (4); wherein
formula (2) is

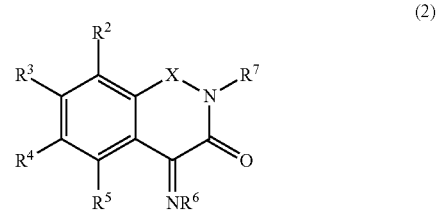

wherein each of $R^2$ to $R^5$ independently represents a hydrogen atom, an alkoxy group, or an alkyl group containing 1 to 10 carbon atoms; $R^6$ represents a hydrogen atom, a hydroxyl group, an alkoxy group, an aryloxy group, an amino group, or an alkyl group or an aryl group containing 1 to 10 carbon atoms; $R^7$ represents a hydrogen atom or an alkyl group containing 1 to 10 carbon atoms; and X represents an ethylene group or an arylene group, and formula (4) is

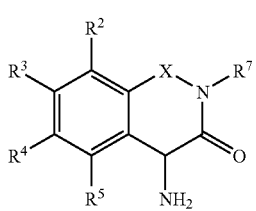

(4)

wherein $R^2$ to $R^5$, $R^7$, and X have the same definitions as described above.

3. The method according to claim 2, which further comprises resolving the aminobenzazepinone into an optically active aminobenzazepinone.

4. A method for producing a 2-iminocarboxylic acid derivative represented by formula (3) or a salt thereof, which comprises reacting an isoquinoline derivative represented by formula (1) with an amine or a salt thereof; wherein formula (1) is

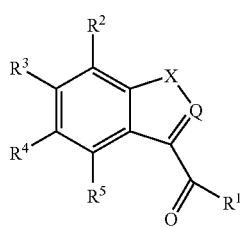

(1)

wherein $R^1$ represents an alkoxy group; each of $R^2$ to $R^5$ independently represents a hydrogen atom, an alkoxy group, or an alkyl group containing 1 to 10 carbon atoms; X represents an ethylene group or an arylene group; and Q is a tertiary or quaternary nitrogen atom, which, in those cases of a quaternary form, is substituted with an alkyl group or an aryl group containing 1 to 10 carbon atoms and has counter ion(s) $Y^-$, wherein $Y^-$ represents a halide ion, an inorganic acid ion, an alkylsulfate ion, a mesylate ion, a tosylate ion, an alkylsulfonate ion, an organic acid ion, and/or a hydroxide ion; and formula (3) is

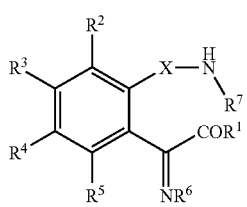

(3)

wherein $R^1$ to $R^5$ and X have the same definitions as described above for formula (1); $R^6$ represents a hydrogen atom, a hydroxyl group, an alkoxy group, an aryloxy group, an amino group, or an alkyl group or an aryl group containing 1 to 10 carbon atoms; and $R^7$ represents a hydrogen atom or an alkyl group containing 1 to 10 carbon atoms.

5. A method for producing a benzazepinone represented by formula (2) or a salt thereof, which comprises lactamizing a 2-iminocarboxylic acid derivative represented by formula (3) or a salt thereof; wherein formula (3) is

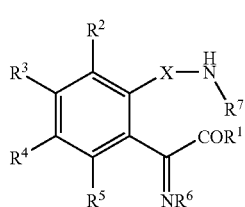

(3)

wherein $R^1$ represents an alkoxy group; each of $R^2$ to $R^5$ independently represents a hydrogen atom, an alkoxy group, or an alkyl group containing 1 to 10 carbon atoms; $R^6$ represents a hydrogen atom, a hydroxyl group, an alkoxy group, an aryloxy group, an amino group, or an alkyl group or an aryl group containing 1 to 10 carbon atoms; $R^7$ represents a hydrogen atom or an alkyl group containing 1 to 10 carbon atoms; and X represents an ethylene group or an arylene group; and formula (2) is

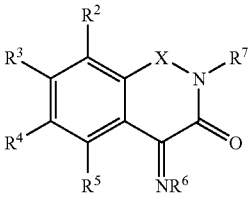

(2)

wherein $R^2$ to $R^7$ and X have the same definitions as described above.

6. A 2-iminocarboxylic acid derivative represented by formula (3) or a salt thereof

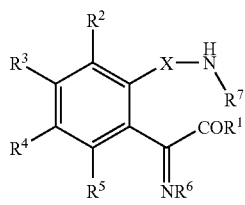

(3)

wherein $R^1$ represents an alkoxy group; each of $R^2$ to $R^5$ independently represents a hydrogen atom, an alkoxy group, or an alkyl group containing 1 to 10 carbon atoms; $R^6$ represents a hydrogen atom, a hydroxyl group, an alkoxy group, an aryloxy group, an amino group, or an alkyl group or an aryl group containing 1 to 10 carbon atoms; $R^7$ represents a hydrogen atom or an alkyl group containing 1 to 10 carbon atoms; and X represents an ethylene group or an arylene group.

7. A 3,4-dihydroisoquinolinium salt represented by formula (1a):
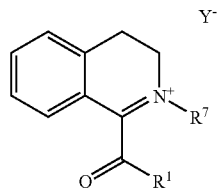
wherein $R^1$ represents an alkoxy group; $R^7$ represents a hydrogen atom or an alkyl group containing 1 to 10 carbon atoms; and $Y^-$ represents a halide ion, an inorganic acid ion, an alkylsulfate ion, a mesylate ion, a tosylate ion, an alkylsulfonate ion, an organic acid ion, and/or a hydroxide ion.
* * * * *